(12) United States Patent
Chen et al.

(10) Patent No.: US 7,547,381 B2
(45) Date of Patent: Jun. 16, 2009

(54) SENSOR ARRAY INTEGRATED ELECTROCHEMICAL CHIP, METHOD OF FORMING SAME, AND ELECTRODE COATING

(75) Inventors: Yu Chen, Singapore (SG); Jianshan Ye, Singapore (SG); Fwu-Shan Sheu, Singapore (SG); Hui Fang Cui, Zhengzhou (CN); Ser Choong Chong, Singapore (SG)

(73) Assignee: Agency for Science, Technology and Research and National University of Singapore, Singapore (SG)

( * ) Notice: Subject to any disclaimer, the term of this patent is extended or adjusted under 35 U.S.C. 154(b) by 769 days.

(21) Appl. No.: 10/672,366

(22) Filed: Sep. 26, 2003

(65) Prior Publication Data
US 2005/0067279 A1 Mar. 31, 2005

(51) Int. Cl.
G01N 27/403 (2006.01)
(52) U.S. Cl. ...................... 205/766; 204/412
(58) Field of Classification Search ............ 204/403.13, 204/412; 438/1
See application file for complete search history.

(56) References Cited

U.S. PATENT DOCUMENTS

| | | | |
|---|---|---|---|
| 4,225,410 A | 9/1980 | Pace | |
| 4,837,049 A | 6/1989 | Byers et al. | |
| 4,874,499 A | 10/1989 | Smith et al. | |
| 5,120,421 A | 6/1992 | Glass et al. | |
| 5,620,579 A * | 4/1997 | Genshaw et al. | 204/402 |
| 5,670,031 A * | 9/1997 | Hintsche et al. | 205/777.5 |
| 5,756,355 A | 5/1998 | Lang et al. | |
| 6,017,440 A | 1/2000 | Lewis et al. | |
| 6,054,039 A | 4/2000 | Shieh | |
| 6,090,933 A * | 7/2000 | Kayyem et al. | 536/25.3 |
| 6,277,629 B1 | 8/2001 | Wolf et al. | |
| 6,315,940 B1 | 11/2001 | Nisch et al. | |
| 6,503,847 B2 | 1/2003 | Chen et al. | |

(Continued)

FOREIGN PATENT DOCUMENTS

GB 2313912 A 12/1997

(Continued)

OTHER PUBLICATIONS

Cui, Xiaoli; Dianlu Jiang; Peng Diao; Jumxin Li; Ruting Tong; Xinkui Wang; Electron transfer between ferrocene-modified Au/octadecanethiol/lipid BLM electrode and redox couples in solution; 1999; Elsevier; 48; 243-247.*

(Continued)

Primary Examiner—Kaj K Olsen
(74) Attorney, Agent, or Firm—Klarquist Sparkman, LLP

(57) ABSTRACT

A sensor array integrated electrochemical chip is provided wherein the chip has an array of electrodes. The array may be formed on a base plate bonded to a cover plate having an opening. The opening can be a window or a depression. The plates are bounded such that they define a cavity, with the array being within the cavity. Conducting lines for connecting the electrodes to electrochemical instruments may be formed on the same surface of the base plate on which the electrodes are formed. At least one of the electrodes may be covered by a coating doped with a ferrocene compound. The coating may be a supported bilayer lipid membrane doped with benzoyl-ferrocene. The doped ferrocene compound may be oxidized.

17 Claims, 4 Drawing Sheets

U.S. PATENT DOCUMENTS

| | | | |
|---|---|---|---|
| 6,540,891 B1 * | 4/2003 | Stewart et al. | 204/403.14 |
| 6,596,143 B1 | 7/2003 | Wang et al. | |
| 2002/0074227 A1 | 6/2002 | Nisch et al. | |
| 2002/0081588 A1 | 6/2002 | De Lumley-woodyear et al. | |
| 2002/0090649 A1 * | 7/2002 | Chan et al. | 435/7.1 |
| 2003/0009112 A1 | 1/2003 | Hammerle et al. | |
| 2003/0217918 A1 * | 11/2003 | Davies et al. | 204/403.02 |
| 2004/0000483 A1 * | 1/2004 | Jackson et al. | 204/601 |
| 2004/0126814 A1 * | 7/2004 | Singh et al. | 435/7.1 |
| 2004/0248282 A1 * | 12/2004 | Sobha M. et al. | 435/287.2 |
| 2006/0121287 A1 * | 6/2006 | Nelson et al. | 428/411.1 |

FOREIGN PATENT DOCUMENTS

WO     WO 2004/048603 A2     6/2004

OTHER PUBLICATIONS

Cui et al., "Electron transfer between ferrocene-modified Au/octadecanethiol/lipid BLM electrode and redox couples in solution", in Bioelectrochemistry and Bioenergetics, 1999, vol. 48, pp. 243-247, Elsevier Science S.A.

Peter Fromherz et al.; Silicon-Neuron Junction: Capacitive Stimulation of an Individual Neuron on a Silicon Chip; Physical Review Letters, Aug. 1995, p. 1670-16, vol. 75 No. 8.

Joseph Wang; Electrochemical nucleic acid biosensors; Analytica Chimica Acta, Sep. 2002, p. 63-71, vol. 469, Elsevier.

H. T. Tien et al.; Supported Bilayer Lipid Membranes as Ion and Molecular Probes; Analytical Sciences, Feb. 1998, p. 3-18, vol. 14, Japan.

Wen Jin et al.; Properties and applications of proteins encapsulated within sol-gel derived materials; Analytical Chimica Acta, Jun. 2002, p. 1-36, vol. 461, Elsevier.

Rolf Weis et al.; Neuron Adhesion on a Silicon Chip Probed by an Array of Field-Effect Transistors; Physical Review Letters, Jan. 1996, p. 327-330, V.76, No. 2.

* cited by examiner

SENSOR ARRAY INTEGRATED ELECTROCHEMICAL CHIP, METHOD OF FORMING SAME, AND ELECTRODE COATING

The present invention relates to sensor array integrated electrochemical chips, methods of forming same, and electrode coatings.

Electrochemical sensors are useful for detecting the presence of, or measuring the concentration of, a target chemical or biochemical substance in a fluid.

A typical electrochemical sensor has a sensing electrode (also known as working electrode or measuring electrode), and one or both of a counter electrode (also known as auxiliary electrode) and a reference electrode. The electrodes are immersed in the fluid containing the target substance during operation. A key process in an electrochemical reaction is the transfer of electrons between the working electrode surface and molecules in the interfacial region (either in the fluid or immobilized at the electrode surface). An electrical signal can be detected if the working electrode is exposed to the target substance. The signal arises due to either a change in potential at the electrode, or a flow of electrons (current) through the electrodes which is generated in response to an imposed voltage signal on the electrodes, as a result of the reduction-oxidation reactions, known as redox reactions, occurring at the electrode surfaces.

An electrode of a sensor may be covered by a coating to control the properties, selectivity and sensitivity of the sensor. For example, it is sometimes desirable to control the electrical resistance at the electrode-fluid interface. The resistance at the interface affects the current response of the electrode, because it affects the permeability of electrolytes that reach the electrode, and consequently the signal/noise ratio. In this regard, metal supported bilayer lipid membranes (s-BLM) have been used as a coating on electrodes. See e.g., Tien et al., "Supported Bilayer Lipid Membranes as Ion and Molecular Probes", Analytical Sciences, (1998), vol. 14, p. 3. However, known s-BLM coatings only provide a limited increase in electrical resistance. Further, with known s-BLM coatings, it is difficult to obtain a stable specific resistance, as the resistance of the coating material is not easily controllable and the formed coating can be damaged due to rugged laboratory handling.

Sensor array integrated devices are useful as they are compact and can be used to simultaneously analyze the same component at different measuring points or different components of a sample. A number of techniques have been used to form electrochemical sensor array integrated devices. For example, U.S. Pat. No. 6,315,940 to Nisch el al. discloses a microelement device having a base plate and a cover plate, wherein the cover plate has multiple microcuvettes, each of which encloses a sensing electrode formed inside a microcuvette of the cover plate, or on top of the base plate, or in a third plate sandwiched between the cover plate and the base plate. These existing techniques, however, have drawbacks, such as a relatively complicated process for the fabrication of the integrated devices.

Therefore, there remains a need for an improved electrode coating, and improved approaches to forming electrodes and sensor array integrated electrochemical chips.

SUMMARY OF THE INVENTION

A sensor array integrated electrochemical chip is provided wherein the chip has an array of electrodes. At least one of the electrodes may be covered by a coating doped with a ferrocene compound. The array may be formed on a base plate bonded to a cover plate having an opening such that the array is within a cavity defined by the base plate and the cover plate. Conducting lines for connecting the electrodes to electrochemical instruments may be formed on the same surface of the base plate on which the electrodes are formed.

In accordance with one aspect of the invention, there is provided a sensor array integrated electrochemical chip comprising an array of electrodes, at least one electrode of the array of electrodes being covered by a coating doped with a ferrocene compound.

In accordance with another aspect of the invention, there is provided a method of forming an electrochemical chip, comprising forming a first plate by depositing a conducting layer on a first support and etching the conducting layer to form an electrode array; forming a second plate by etching an opening in a second support; and bonding the second plate to the first plate such that the first plate and the second plate define a cavity, with the electrode array being within the cavity. The opening may be a window or a depression. The method may further comprising covering at least one electrode of the electrode array with a coating doped with a ferrocene compound. The method may further comprising oxidizing the ferrocene compound.

In accordance with yet another aspect of the invention there is provided a method of forming an electrochemical chip comprising forming a metal array; and covering at least some elements of the array with a supported bilayer lipid membrane doped with a ferrocene compound.

In accordance with still another aspect of the invention there is provided a method of using a ferrocene compound as a dopant in an electrode coating.

In accordance with yet another aspect of the invention there is provided a sensor array integrated electrochemical chip, comprising a first plate having an array of electrodes thereon and a second plate having an opening, the second plate bonded to the first plate so that the first plate and the second plate define a cavity, with the array of electrodes being within the cavity. The opening may be a window or a depression. The first plate may have a plurality of conducting lines formed on a same surface of the first plate on which the array of electrodes is formed, each of the conducting lines extending from one of the electrodes outwardly beyond a periphery of the array.

Other aspects, features and advantages of the invention will become apparent to those of ordinary skill in the art upon review of the following description of specific embodiments of the invention in conjunction with the accompanying figures.

BRIEF DESCRIPTION OF THE DRAWINGS

In the figures, which illustrate exemplary embodiments of the invention.

DETAILED DESCRIPTION

When used herein:

"array of electrodes" means at least two electrodes formed in any pattern. The electrodes can be either interconnected or independently wired.

"sensor array" means an array of sensors which can consist of identical or different sensors.

"bonded" means held together, either chemically or mechanically, or otherwise.

"ferrocene compound" means a chemical compound containing a ferrocene group. A ferrocene group has the chemical formula $C_5H_5FeC_5H_4$—. Examples of ferrocene compounds include ferrocene ($C_5H_5FeC_5H_5$) and benzoylferrocene ($C_5H_5FeC_5H_4COC_6H_5$).

In overview, a sensor array integrated electrochemical chip may have an array of electrodes. At least one of the electrodes may be covered by a coating doped with a ferrocene compound, such as a supported bilayer lipid membrane (s-BLM) doped with benzoylferrocene. The electrodes may be formed on a base plate, which is bonded to a cover plate having an opening such that such that the array is within a cavity defined by the base plate and the cover plate. The opening of the cover plate may be a window or a depression. The electrodes may be interconnected or independently wired. The electrodes and the connecting lines may be formed on the same surface of the base plate.

The ferrocene doped coating has high electrical resistance. Thus, the resistance at the coated electrodes is higher compared to un-coated electrodes or electrodes coated with a conventional undoped s-BLM. The increase in electrical resistance of the coating covering the electrodes can be controlled by both the doping concentration and the degree of oxidization of the ferrocene compound. In this regard, it has been discovered that oxidizing the doped ferrocene compound increases resistance. With an appropriate resistance, the signal-to-noise ratio of the sensor can be increased.

Figure 1:
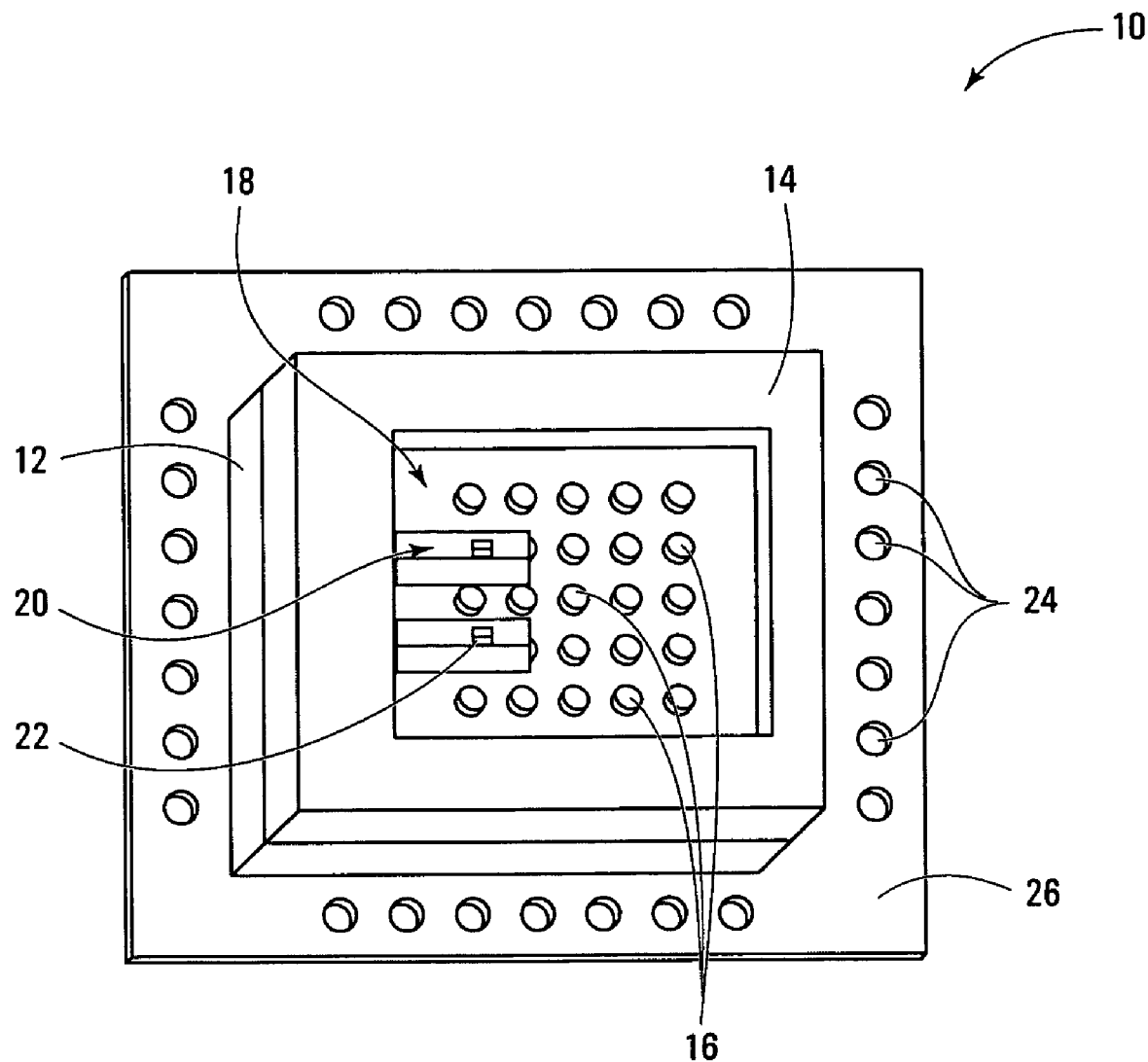
FIG. 1 is a schematic perspective view of a sensor array integrated electrochemical chip.
Figure 2:
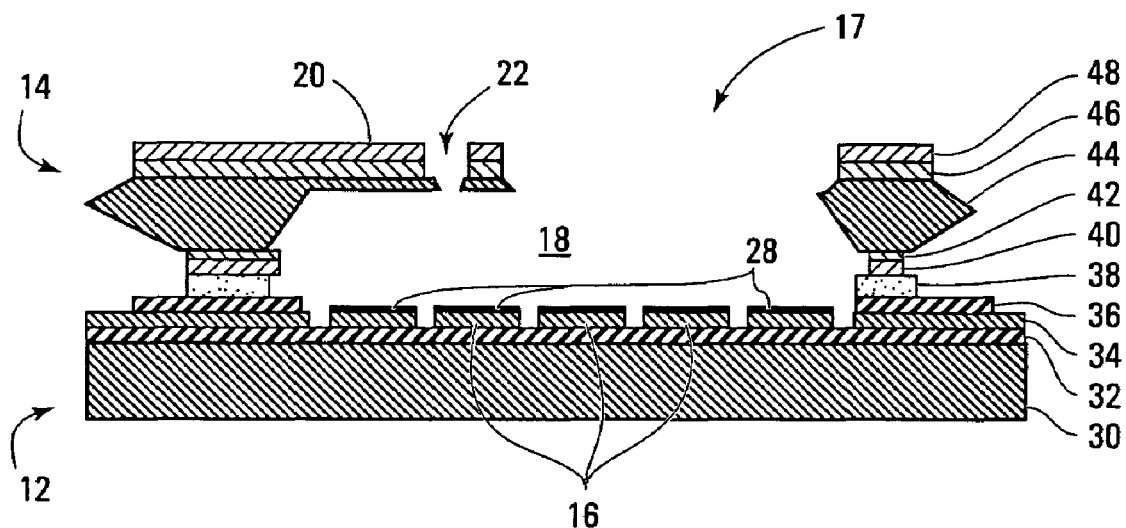
FIG. 2 is a schematic partial cross-sectional view of the electrochemical chip of FIG. 1.

FIGS. 1 and 2 illustrate schematically an electrochemical chip 10 having a base plate 12 and a cover plate 14. An array of electrodes 16 is formed on base plate 12. Cover plate 14 has an opening, window 17. Base plate 12 and cover plate 14 together define a cavity, reaction chamber 18, such that the array of electrodes 16 is within reaction chamber 18.

Optionally, one or more cantilevers 20 can be provided on cover plate 14 as support for external electrodes (not shown), such as an external counter or reference electrode, or both. Each external electrode may be inserted into an opening 22 in a cantilever 20 and extended into reaction chamber 18.

Electrodes 16 may all be working electrodes, or may include one or more counter electrodes and/or reference electrodes. Each electrode 16 may be individually electrically controlled through contact holes 24 on printed circuit board (PCB) 26. PCB 26 provides electrical input/output connections to external electrical and/or electronic instruments. As will be understood by a person skilled in the art, bond pads and conducting lines (also known as "runners") are typically used for connecting the electrodes to contact holes 24. External instruments may be connected to the electrodes via contact holes 24. Alternatively, the bond pads and conducting lines could directly connect the electrodes to external instruments. The bond pads and the conducting lines can also be formed on the base plate 12. However, for clarity, the bond pads and conducting lines connecting electrodes 16 to contact holes 24 are not shown in FIG. 1 (but shown in FIG. 7).

Electrochemical chip 10 may have various sizes and shapes suitable for particular applications. For example, electrochemical chip 10 may have a chip size varying from 1×1 cm to 2×2.25 cm and a chamber area varying from 6×6 mm to 2×44 mm.

While an array of 5×5 electrodes is shown in FIG. 1, the array of electrodes 16 may have any suitable pattern or number of electrodes depending on the application. Electrodes 16 may have various shapes, such as square, rectangular, circular, ovoid, and the like. Electrodes 16 may also have various sizes and can be made very small, such as less than 90 μm in length and width. Diameters from 10 μm to 90 μm have been tested and were found to be suitable. Typically, each working electrode may have a surface area in the range of $1 \times 10^{-7}$ to $1 \times 10^{-4}$ cm$^2$ or less. Smaller sizes may be preferable in many biochemical applications. Electrodes 16 may be evenly or unevenly spaced with various inter-electrode distances depending on the application. For example, inter-electrode distances in the range of 10 to 100 μm were found suitable in an exemplary electrochemical chip. The pixel sizes of chip 10 may also vary. Pixels with a length of 0.25 mm were found suitable in an exemplary electrochemical chip.

As illustrated in FIG. 2, base plate 12 may be bonded to cover plate 14 by a bonding material 38.

Base plate 12 includes base wafer 30, first insulation layer 32, conducting layer 34, and second insulation layer 36. Wafer 30 may be made of silicon, or other suitable material such as glass, plastic, polymer sheet, ceramic and semiconductor materials. Insulation layers 32 and 36 may be made of the same or different materials. Suitable material for insulation layers 32 and 36 include silicon dioxide, silicon nitride, and other suitable organic and inorganic materials. For use in biochemical applications, the exposed materials (uncovered portions of wafer 44 and layers 32 and 36) should be compatible with the intended electrolytes and biological or biochemical testing solutions. Insulation layers 32 and 36 should be thick enough to provide sufficient insulation. Each of insulation layers 32 and 36 may have a thickness in the range of 0.1 to 5 μm. Conducting layer 34 may comprise suitable conducting material, such as Cr, Au and Ti, and may itself be layered. For example, conducting layer 34 may be formed by a layer of Au on top of a layer of Cr or Ti. Electrode array 16 is formed from conducting layer 34. The aforesaid conducting lines for connecting the electrodes to external instruments may also be formed from conducting layer 34. At least one electrode 16 may be covered by a coating 28 doped with a ferrocene compound, such as a benzoylferrocene doped s-BLM. If desired, some or all of electrodes 16 may be covered by a ferrocene doped coating.

Cover plate 14 includes wafer 44 and mask layers 40, 42, 46, and 48. Like wafer 30, wafer 44 may be made of silicon or other suitable material. Mask layers 40, 42, 46, and 48 are deposited on wafer 44 to mask wafer 44 during etching. If wafer 44 is to be etched with a wet chemical method, two mask layers may be deposited on each side of wafer 44, as shown in FIG. 2. The inner mask layers 42 and 46 may be thermal oxide layers and the outer mask layers 40 and 48 may be silicon nitride layers deposited by low pressure chemical vapour deposition. Layers 42 and 46 may be 0.03 to 1 μm thick. Layers 40 and 48 may be 0.1 to 2 μm thick. If wafer 44 is to be etched with a dry etching method, a single mask layer on each side may be sufficient. The single mask layer may be formed with materials such as photoresist, silicon oxide, silicon nitride, and any other materials suitable for dry etching. One or more of mask layers 40, 42, 46, and 48 may be removed after etching. However, to simplify the fabrication process, the mask layers may be kept intact.

Example approaches to forming base plate 12 and cover plate 14 are illustrated in FIG. 3A to 3C and 4A to 4D.

Figure 3A:
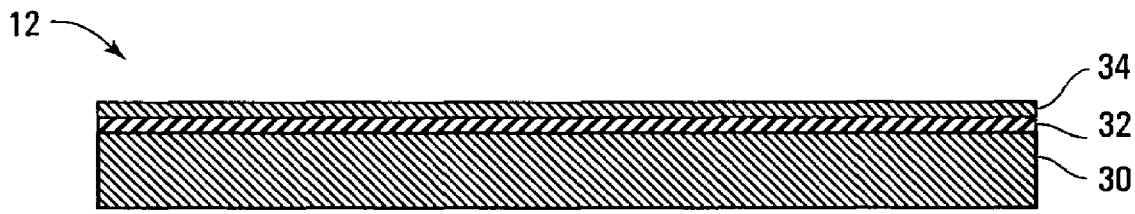
FIG. 3A-3C schematically illustrate an approach to forming the base plate of FIG. 1.

Referring to FIG. 3A, insulation layer 32 is deposited onto silicon wafer 30 to form a support. Conducting layer 34 is next deposited onto insulation layer 32. Any suitable deposition technique can be used.

Figure 3B:
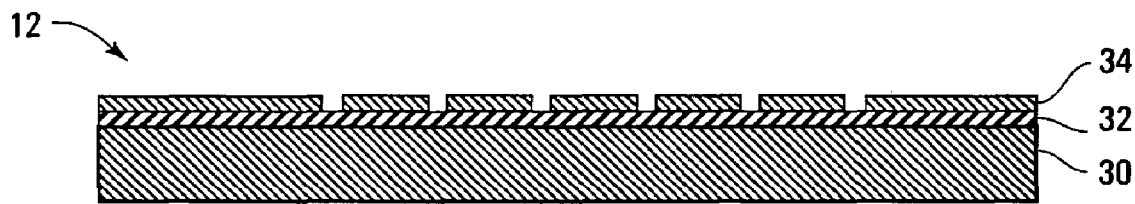

Referring to FIG. 3B, conducting layer 34 is then patterned and etched to form electrode array 16, bond pads, and circuit lines connecting each electrode to a bond pad. Standard semiconductor microfabrication techniques such as lithograph techniques may be used.

Figure 3C:
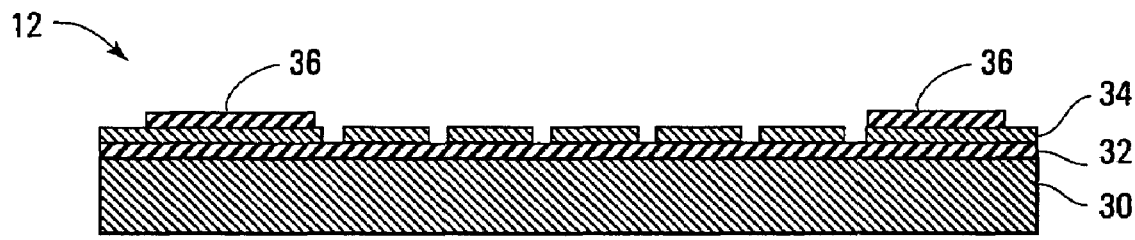

Referring to FIG. 3C, insulation layer 36 is next deposited onto conducting layer 34. Layer 36 is then etched to expose electrode array 16 and bond pads. Layer 36 can be etched with any suitable etching technique such as plasma dry etching or wet chemical etching. Layer 36 is not etched away in the area around a periphery of the electrode array 16 where the two bonded plates will be in contact. As illustrated in FIG. 2, cover plate 14 will be bonded to base plate 12 at the remaining insulation layer 36 which abuts cover plate 14.

Figure 4A:
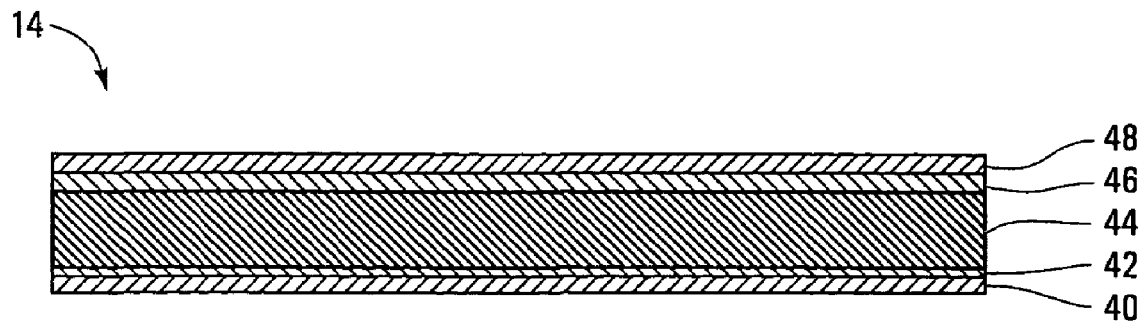
FIG. 4A-4D schematically illustrate an approach to forming the cover plate of FIG. 1.

Referring to FIG. 4A, a support for forming cover plate 14 is formed by depositing, sequentially, mask layers 42 and 46 and then mask layers 40 and 48 on both sides of wafer 44. Wafer 44 may be made of silicon. The insulation layers may be formed using a low pressure chemical vapor deposition technique.

Figure 4B:
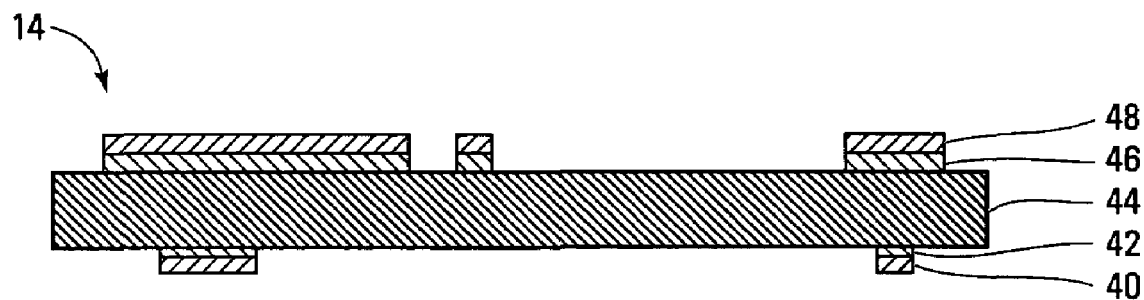

Referring to FIG. 4B, the window area for reaction chamber 18, the areas for bond pads, and areas for cantilevers 20 are etched out from layers 40, 42, 46 and 48, using standard semiconductor microfabrication techniques such as lithograph techniques, to expose wafer 44 in these areas.

Figure 4C:
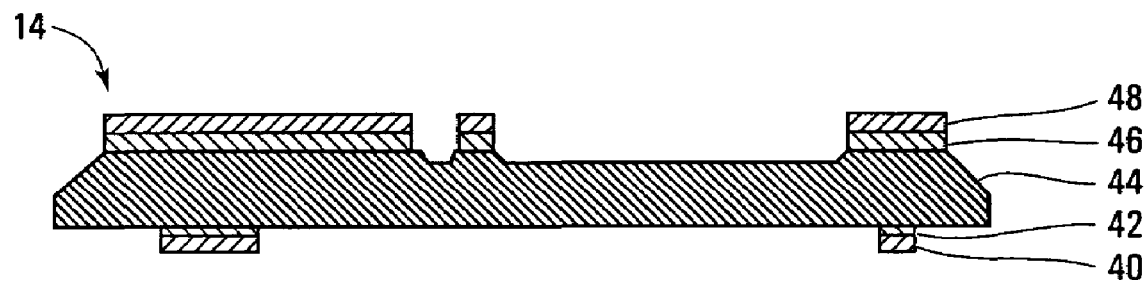
Figure 4D:
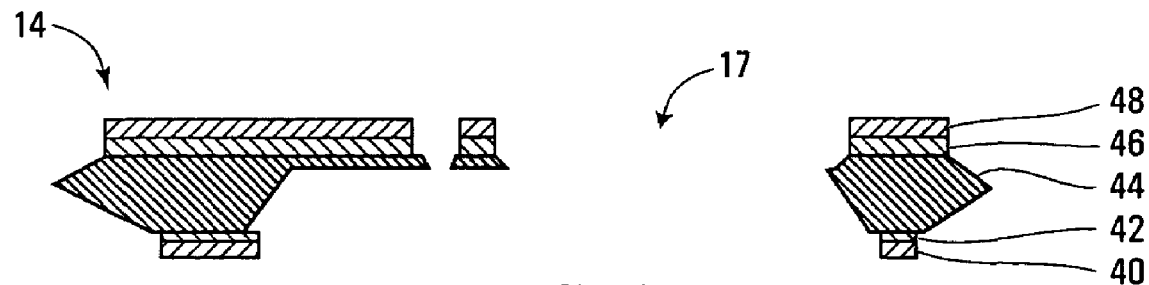

Referring to FIG. 4C, wafer 44 is etched from the front side (top side in the figures), which will face away from base plate 12 when cover plate 14 is bonded to base plate 12. More than 10 µm thick of wafer 44 may be etched away within the open areas. Referring to FIG. 4D, wafer 44 is then etched through from the backside (bottom side in the figures), which will face base plate 12 when cover plate 14 is bonded to base plate 12. The side exterior of wafer 44 may also be etched to expose the bond pads. To etch wafer 44, techniques such as KOH wet chemical etching or silicon dry etching may be used.

As noted above, one or more of mask layers 40, 42, 46, and 48 may be removed after etching.

Returning to FIG. 2, base plate 12 and cover plate 14 can then be bonded together, with window 17 of cover plate 14 over electrode array 16, using techniques such as taught by U.S. Pat. No. 6,503,847 to Chen et al. ("Chen") issued Jan. 7, 2003, the contents of which are incorporated herein by reference. In particular, diluted polydimethylsiloxane (PDMS) solutions may be prepared as taught in Chen. The surface of layer 40 (or the backside of wafer 44 if mask layers 40 and 42 have been removed) is then spin coated with PDMS. The PDMS coating may have a thickness in the range of 1 to 500 µm. During the coating process, the front side of wafer 44 may be laminated with polymer film to prevent them from being coated by PDMS. The PDMS may be pre-cured to half curing before cover plate 14 is aligned to base plate 12 and the two plates are pressed toward each other until the PDMS is fully cured. As can be understood, although not shown in FIG. 2 (for clarity), the backside of cover plate 14 and the inner surfaces of window 17 are covered with a layer of PDMS after bonding. Conveniently, the PDMS layer is a biocompatible material so that even if wafer 30 and the mask layers are not biocompatible, chip 10 may still be biocompatible.

As can be appreciated, more than one pair of base and cover plates can be formed simultaneously from two sheets of wafer. If more than one pair is formed, individual pairs can be cut out after the PDMS is fully cured, such as by dicing. Each pair may then be wire bonded to a PCB.

As mentioned, one or more electrodes 16 are covered by a ferrocene compound doped coating, such as a benzoylferrocene doped s-BLM. The coating may be deposited on an electrode 16 in various ways. An exemplary procedure for covering an electrode 16 with a benzoyferrocene doped s-BLM is as follows:

Dissolve benzoylferrocene and dimyristoyl L-α-phosphatidylcholine (DMPC) in analytical grade chloroform to prepare a lipid solution wherein the concentrations of benzoylferrocene and DMPC are in the range of 0.1 to 10 mg/ml. For example, they may respectively be 1 mg/ml and 2 mg/ml.

Clean electrochemical chip 10. For example, sonicate chip 10 successively in alcohol and de-ionized water for 5 minutes each and then dry chip 10 in air;

Apply the lipid solution onto the surface of the electrode in small quantities, such as drop 20 µl aliquots of the lipid solution with a microsyringe;

Evaporate chloroform on the electrode gradually in air at room temperature;

Transfer 1 ml of phosphate buffer solution (PBS) onto the lipid-coated electrode 16, wherein the buffer solution may contain 8 g/l NaCl, 0.2 g/l KCl, 1.44 g/l $Na_2HPO_4$, 0.24 g/$KH_2PO_4$, with a pH value of 7.4. The buffer solution can also be any suitable neutral aqueous solution in which the lipid bilayer membrane is stable.

Other suitable doping procedures, such as absorption and diffusion doping methods may also be employed. It will be appreciated, however, that the doping process should not negatively affect the s-BLM properties.

As can be appreciated, a benzoylferrocene doped s-BLM will form spontaneously (by molecular self-assembling) in the PBS solution on the electrode.

Test results have shown that the electrical resistance of an s-BLM coating is higher when doped with benzoylferrocene than without doping. Test results also show that electrical resistance can be further increased if the doped benzoylferrocene is oxidized.

Benzoylferrocene in the coated s-BLM can be oxidized by subjecting the electrodes 16 to cyclic potential changes for example from −0.3 to +0.8 V when they are immersed in an electrolytic solution such as a PBS containing potassium ferricyanide ($K_3[Fe(CN)_6]$), whereby redox reactions occur on the coating.

Whether or not benzoylferrocene in the coating has been oxidized can be readily tested by examining the electrode's current response to redox reactions. When the current response is small, it has been oxidized. If the current response is large, then it has not been fully oxidized.

Conveniently, the electrical resistance at electrodes 16 can be controlled by controlling the degree of oxidization of benzoylferrocene in the s-BLM coating. Furthermore, test results show that the oxidization of benzoylferrocene is irreversible. That is, once oxidized, the benzoylferrocene will remain oxidized, thus providing a stable electrical resistance at the electrode interfaces. (However, if the benzoylferrocene is not fully oxidized, it may become further oxidized if the potential applied to the electrodes is higher than the oxidation potential.)

The resistance of the coating can also be controlled by adjusting the dopant concentration.

Other ferrocene compounds may also be used to dope the s-BLM coating. For example, ferrocene ($C_5H_5FeC_5H_5$) or 1,1'[(4,4'-Bipiperidine)-1,1'-diyldicarbonyl]-bis[1'-(methoxycarbonyl)ferrocene] may be used.

Further, s-BLM may be replaced by other materials such as any suitable organic polymers or membranes that can be modified, immobilized, or self-assembled at the surface of electrodes 16 and doped with a ferrocene containing compound. Advantageously, the doped lipid membrane retains its biocompatible microenvironment in the presence of enzymes, thus the sensor is suitable for biochemical applications.

The coating may be permeable or impermeable, depending on the type of sensing mechanism to be employed. For example, a permeable coating may be used for amperemetry-type sensors while an impermeable coating may be used for resistance or impedance-type sensors.

It is also possible to cover different electrodes 16 with different coatings, such as coatings comprising different materials or similar materials having different oxidization states.

In operation, electrochemical chip 10 is wired to external control and data taking instruments, through contact holes 24. Reaction chamber 18 is filled with a liquid. The electrodes are biased in a typical manner for an electrochemical sensor or a sensor array so that electrical signals can be detected to determine if, and/or how fast, a certain redox reaction occurs in the fluid. Thus, whether one or more particular target substances are present in the fluid, or the concentrations of the substances, can be determined. When required, one or both of an external counter electrode and an external reference electrode supported by cantilevers 20 may be used. Electrodes 16 may be all used as working electrodes. Or, one or more of electrodes 16 may be used as counter or reference electrodes.

As can be appreciated, electrochemical chip 10 is easy to fabricate. The two-plate structure makes it easy to form electrode array 16 since conducting layer 34 can be deposited onto a flat surface and then etched away to form individual electrodes. Similarly, other metal components such as bond pads and connection lines are easily formed. A large reaction chamber 18 is also possible, as it can be as deep as the full thickness of wafer 44. Since two wafers are used, more electronic devices may be fit onto electrochemical chip 10 than onto a single wafer chip.

Conveniently, all electrodes, including working electrodes, counter electrodes, and reference electrodes, can be formed with the same material on the same conducting layer 34. Optional counter electrodes and reference electrodes made of different materials may nonetheless be provided and supported by cantilevers 20.

As all the electrodes 16 are located in one reaction chamber 18, simultaneous sensing or testing is possible, which reduces sample usage and analyzing time. Multiple components of the same sample can be tested at the same time. Alternatively, data obtained from multiple electrodes can be combined to arrive at a more accurate or reliable results.

As can be appreciated, even without coating the electrodes with a coating doped with a ferrocene compound, forming an electrochemical chip as taught herein is still advantageous since the fabrication process is simple and inexpensive.

Electrochemical chip 10 may also be used in applications other than electrochemical sensing. For example, the electrodes can be used for AC or DC electrical measurements.

Other features, benefits and advantages of the present invention not expressly mentioned above can be understood from this description and the accompanying drawings by those skilled in the art.

As can be understood by a person skilled in the art, many modifications to the exemplary embodiments of the invention described herein are possible. For example, conducting layer 34 (and hence electrodes 16) may be made of any suitable metals or metal alloys such as Au, Pt, Ag, indium tin oxide (ITO), and the like, or conductive polymers. Insulating materials for layers 32, 36 can be any suitable type of insulating polymers. Bonding material for layer 38 can be any suitable biocompatible and chemically resistive material.

Base plate 12 and cover plate 14 need not be chemically bonded. They can be simply stacked and mechanically held so that reaction chamber 18 is leak-proof, in which case bonding layer 38 may be omitted.

Figure 5:
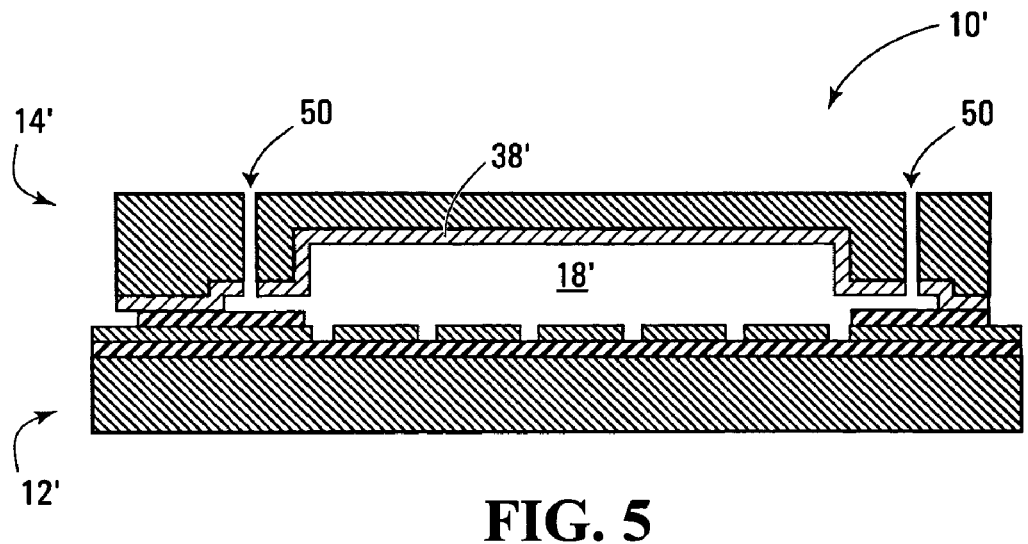
FIG. 5 is a schematic partial cross-sectional view of another sensor array integrated electrochemical chip.

Further, cover plate 14 may have a window shape different from the one shown in FIGS. 2 and 4A-4D. For instance, the window on the cover plate may have a shape other than a square when viewed from the front side. Further, the window on the cover plate need not be completely open. For example, FIG. 5 illustrates another sensor array integrated electrochemical chip 10', wherein the opening in cover plate 14' is etched only half-way through thus forming a depression. Cover plate 14 and base plate 12' are bonded together to define a cavity, reaction chamber 18'. Sample liquids can flow through channels 50 in cover plate 14' into and out of reaction chamber 18'. The entire backside of cover plate 14' and the side walls of reaction chamber 18' may be coated with a biocompatible material 38' such as PDMS and the like.

Figure 6:
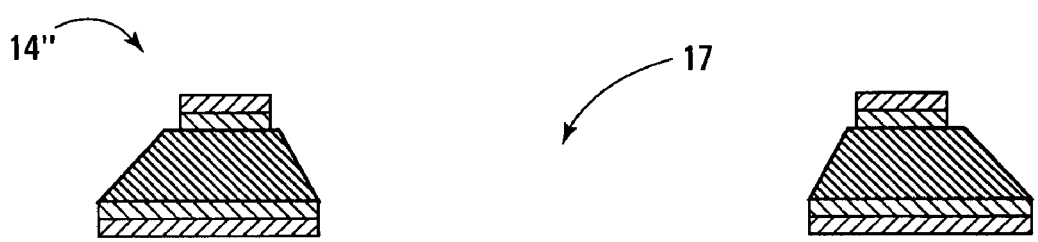
FIG. 6 is a schematic partial cross-sectional view of a cover plate.

Another alternative cover plate 14", which has no cantilever, is illustrated in FIG. 6. The silicon wafer of cover plate 14" may be etched either from top or from bottom.

Electrodes 16 may also be formed on the side walls of reaction chamber 18, if desired.

Figure 7:
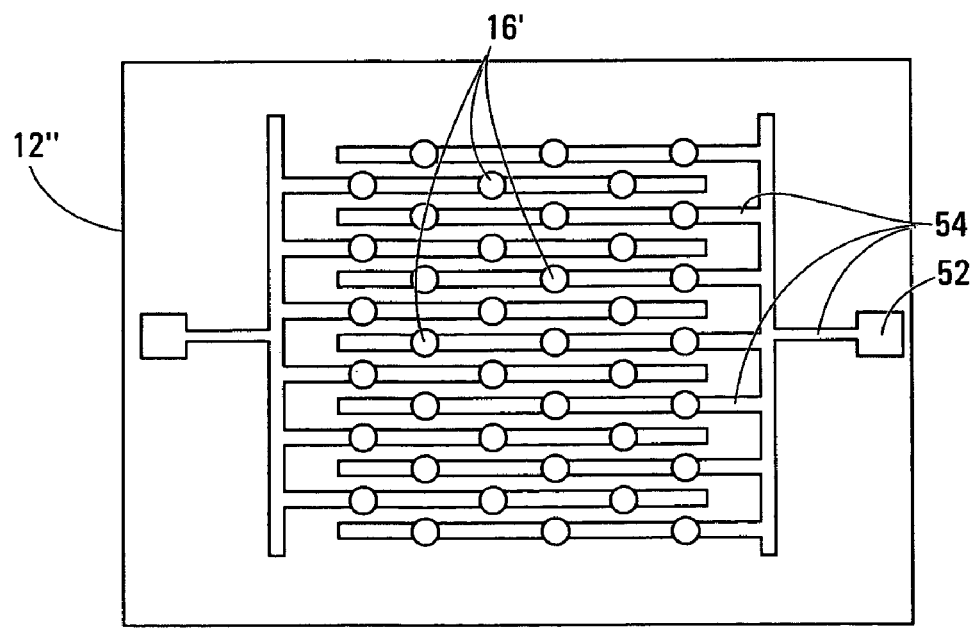
FIG. 7 is a partial plan view of an electrode array on a base plate.

As illustrated in FIG. 7, electrodes 16' may also be interconnected in parallel and grouped into two or more groups and each group of electrodes be connected to a common bond pad 52 through conducting lines 54. As illustrated, each of the conducting lines extends from an electrode outwardly beyond a periphery of the electrode array.

If the base and cover plates are bonded with a bonding material that is not biocompatible, a layer of biocompatible, chemically inert material may be deposited on the side walls of the window of the cover plate before it is bonded to the base plate so as to provide biocompatible inner surfaces in the reaction chamber.

The invention, rather, is intended to encompass all such modification within its scope, as defined by the claims.

What is claimed is:

1. A method of forming an electrochemical chip, comprising:
   forming a first plate by:
      depositing a conducting layer on a first support; and
      etching said conducting layer to form an electrode array;
      covering at least one electrode of said electrode array with a coating doped with a ferrocene compound;
      irreversibly oxidizing said ferrocene compound during said forming said electrochemical chip;
   forming a second plate by:
      etching an opening in a second support;
   bonding said second plate to said first plate such that said first plate and said second plate define a cavity, with said electrode array being within said cavity.

2. The method of claim 1 further comprising etching said conducting layer to form a plurality of conducting lines, each of said conducting lines extending from an electrode of said electrode array outwardly beyond a periphery of said electrode array.

3. The method of claim 1 further comprising forming said first support by depositing an insulation layer on a silicon wafer.

4. The method of claim 3 further comprising depositing an overlying insulation layer over said conducting layer about a periphery of said array, said second plate being bonded to said first plate at said overlying insulation layer.

5. The method of claim 1 wherein said second support comprises a silicon wafer.

6. The method of claim 1 further comprising selecting a degree of oxidization and oxidizing said ferrocene compound by said selected degree of oxidization.

7. The method of claim 1 wherein said irreversibly oxidizing said ferrocene compound comprises immersing said at least one electrode in an electrolytic solution after covering said at least one electrode with said coating and cyclically subjecting said at least one electrode to potential changes.

8. The method of claim 7 wherein said ferrocene compound is benzoylferrocene.

9. The method of claim 8 wherein said potential changes cycle between about −0.3 V to +0.8 V.

10. The method of claim 1 wherein said coating is a supported bilayer lipid membrane.

11. The method of claim 1 further comprising selecting a doping concentration for said ferrocene compound and doping said coating with said ferrocene compound to said selected doping concentration.

12. The method of claim 1 wherein said opening is a window.

13. The method of claim 1 wherein said opening is a depression.

14. A method of forming an electrochemical chip, comprising:
    forming a first plate by:
        depositing a conducting layer on a first support; and etching said conducting layer to form an electrode array;
        covering at least one electrode of said electrode array with a coating doped with a ferrocene compound;
    forming a second plate by:
        etching an opening in a second support;
    bonding said second plate to said first plate such that said first plate and said second plate define a cavity, with said electrode array being within said cavity, wherein said coating is a supported bilayer lipid membrane.

15. A method of forming an electrochemical chip, comprising:
    forming a first plate by:
        depositing a conducting layer on a first support; and etching said conducting layer to form an electrode array;
        covering at least one electrode of said electrode array with a coating doped with a ferrocene compound;
    forming a second plate by:
        etching an opening in a second support;
    bonding said second plate to said first plate such that said first plate and said second plate define a cavity, with said electrode array being within said cavity, wherein said ferrocene compound is benzoylferrocene.

16. A method of forming an electrochemical chip, comprising:
    forming a first plate by:
        depositing a conducting layer on a first support; and etching said conducting layer to form an electrode array;
        covering at least one electrode of said electrode array with a coating doped with a ferrocene compound;
        oxidizing said ferrocene compound during said forming said electrochemical chip;
    forming a second plate by:
        etching an opening in a second support;
    bonding said second plate to said first plate such that said first plate and said second plate define a cavity, with said electrode array being within said cavity;
    wherein said oxidizing said ferrocene compound comprises immersing said at least one electrode in an electrolytic solution after covering said at least one electrode with said coating and cyclically subjecting said at least one electrode to potential changes;
    wherein said ferrocene compound is benzoylferrocene.

17. The method of claim 16 wherein said potential changes cycle between about −0.3 V to +0.8 V.

* * * * *